United States Patent [19]

Fujinari et al.

[11] Patent Number: 5,300,441
[45] Date of Patent: Apr. 5, 1994

[54] METHOD FOR MEASURING AND DETERMINING NITROGEN CONTENT IN A SAMPLE AND PROVIDING AN OUTPUT DATA OF TOTAL NITROGEN AND SELECTED CONSTITUENT NITROGEN COMPOUNDS INCLUDING NITRATE AND NITRITE

[75] Inventors: Eugene M. Fujinari, Spring, Tex.; Allen J. Britten, Sydney, Canada

[73] Assignee: Antek Instruments, Inc., Houston, Tex.

[21] Appl. No.: 16,172

[22] Filed: Jan. 21, 1993

Related U.S. Application Data

[63] Continuation of Ser. No. 654,080, Feb. 11, 1989, abandoned.

[51] Int. Cl.$^5$ ............... G01N 21/62; G01N 21/76
[52] U.S. Cl. ....................... 436/110; 436/106; 436/107; 436/114; 436/116; 436/117; 436/118; 436/172
[58] Field of Search ............ 436/106, 107, 110, 114, 436/115, 116, 117, 118, 172

[56] References Cited

U.S. PATENT DOCUMENTS

| | | | |
|---|---|---|---|
| 3,647,387 | 3/1972 | Benson et al. | 436/107 |
| 4,018,562 | 4/1977 | Parks et al. | 436/114 |
| 4,412,006 | 10/1983 | Cox et al. | 436/172 |
| 4,657,744 | 4/1987 | Howard | 436/172 |
| 4,914,037 | 4/1990 | Forster et al. | 436/106 |

FOREIGN PATENT DOCUMENTS 0110895  8/1979  Japan .................. 436/114

OTHER PUBLICATIONS

Nitrogen, Nitrate-Nitrite, EPA Method 353.3 (Spectrophotometric Cadmium Reduction) Storet No. Total 00630, 1974.
Nitrogen, Nitrate-Nitrite. EPA Method 353.2 (Colorimetric, Automated Cadmium Reduction) Storet No. Total 00630, 1978, 1974, 1971.
Standard Methods for Examination of Water adn Waste Water 14th Ed., 1975. 419 LC. Cadmium Reduction Method (Tentative).
P. G. Brewer and J. P. Riley, "The Automatic Determination of Nitrate in Sea Water". Deep-Sea Research, 1965, vol. 12, p. 765.
Robert D. Cox, "Determination of Nitrate and Nitrite at the Parts per Billion Level by Chemiluminescence". Anal. Chem. 1980, 52, 332-335.
Robert C. Doerr, Jay B. Fox, Jr., Leon Lakritz, and Walter Fiddler, "Determination of Nitrite in Cured Meats by Chemiluminescence Detection". Anal. Chem. 1981, 53, 381-384.

(List continued on next page.)

Primary Examiner—James C. Housel
Assistant Examiner—David Redding
Attorney, Agent, or Firm—Donald Gunn

[57] ABSTRACT

A method for analyzing total bound nitrogen in a sample and providing an output data of total bound nitrogen and constituent compounds (nitrate and nitrite) is disclosed. The total nitrogen bound method provides a discrete sample through a furnace in the presence of continuous flow of water as carrier as well as oxygen carrier gas, resulting in the oxidation of the nitrogen compounds to nitric oxide. The nitrate method involves a discrete sample with water as a carrier provided to a sparge tank. The nitrite is catalytically reduced to nitric oxide in the presence of tartaric acid and ascorbic acid. The nitrate method involves a first conversion to change the nitrate to a nitrite. The first conversion occurs in the presence of a copper-cadmium catalyst causing the formation of the $NO_2$. The nitrile is subsequently converted into NO. The nitric oxide produced in each of the three methods is measured in a chemiluminescent nitrogen detector.

15 Claims, 2 Drawing Sheets

OTHER PUBLICATIONS

James E. O'Brien and Janece Fiore, "Automation in Sanitary Chemistry Parts 1 & 2".

F. A. J. Armstrong, C. R. Stearns, and J. D. H. Strickland, "The Measurement of Upwelling and Subsequent Biological Processes By Means of the Technicon Autoanalyzer and Associate Equipment" Deep-Sea Research, 1967, vol. 14, pp. 381–389.

C. Garside, "A Chemiluminescent Technique for the Determination of Nanomolar Concentrations of Nitrate and Nitrite in Seawater" Marine Chemistry, 11 (1982), pp. 159–167.

A. Henriksen and A. R. Selmer-Olsen, "Automatic Methods for Determining Nitrate and Nitrite in Water and Soil Extracts". Analyst, May 1970, vol. 95, pp. 514–518.

Ted W. Walsh, "Total Dissolved Nitrogen in Seawater: a New-High Temperature Combustion Method and a Comparison with Photo-Oxidation". Marine Chemistry, 26 (1989), pp. 295–311.

ASTM Designation: D 1254–67 (reapproved 1974). Standard Methods of Test for Nitrite Ion in Water.

METHOD FOR MEASURING AND DETERMINING NITROGEN CONTENT IN A SAMPLE AND PROVIDING AN OUTPUT DATA OF TOTAL NITROGEN AND SELECTED CONSTITUENT NITROGEN COMPOUNDS INCLUDING NITRATE AND NITRITE

This is a continuation of application Ser. No. 07/654,080 filed Feb. 11, 1989. (abandoned).

BACKGROUND OF THE DISCLOSURE

It is necessary to determine nitrogen in a sample in chemical or laboratory testing circumstances. This is also useful in batch or continuous process control. Such circumstances often call for determination of an output of total bound nitrogen in a particular sample. The term "bound nitrogen" refers to nitrogen which is a chemical constituent of a compound as opposed to free nitrogen. Free nitrogen or diatomic nitrogen, typically found in the atmosphere or disclosed in a sample, is compounded only with the most difficult of efforts; in fact, nitrogen in the atmosphere can be viewed practically as an inert gas which is evidence by the difficulty of reacting diatomic nitrogen with a compound. It is often important to analyze the total nitrogen content of one or more compounds in a sample or specimen where the nitrogen content is important but unknown. This type of measurement can be provided by the equipment and procedure which are set forth in Parks, et al. which is U.S. Pat. No. 4,018,562. In many instances, that analysis is more than sufficient. In other instances, it is important to have an additional break down of the nitrogen content. In other words, a representation that nitrogen represents 100 ppm may be adequate in some circumstances, but in other circumstances, the data must be broken down into specific nitrogen compounds, for instance, nitrites and nitrates are indicated separately. The present disclosure sets forth a method and apparatus for measuring nitrogen constituents in a sample and in particular for providing an indication separating the nitrite component and the nitrate component. In addition, constituents are separated into the most desirable or important nitrogen compounds from the point of view of application and use. Several examples will make this more readily apparent. Consider as one example the analysis of surface water which has washed off a large land area involving farming and ranching. The surface water discharge may carry fertilizer constituents in it. It may be very important to determine the break out of the constituents so that better control of the fertilizer application on the surface area can be executed. In this example, it may be very important to know the nitrate ($NO_3-$) concentration, and to also know the total nitrogen concentration. In another example, a chemical leaching process may discharge waste effluent with nitrites ($NO_2-$) up to a certain specified quantity. This can be tested again by use of the present method and apparatus.

One aspect of the present method and apparatus is that it avoids the wet chemistry approach which has been traditionally known as the Kjeldhal analytical procedure. The Kjeldhal method is inherently time consuming to execute and is relatively expensive. It may also create undesirable waste products. The method of the present disclosure is not a wet chemistry procedure, contrasting with Kjeldhal, and can be executed in a straight forward fashion to provide substantially no waste discharge.

Previously known methods do not provide the desirable procedure of the present disclosure. Several methods are therefore given in the following documents:

1) Nitrogen, Nitrate-Nitrite. EPA Method 353.3 (Spectrophotometric Cadmium Reduction) Storet No. Total 00630, 1974.

2) Nitrogen, Nitrate-Nitrite. EPA Method 353.2 (Colorimetric, Automated, Cadmium Reduction) Storet No. Total 00630, 1978, 1974, 1971.

3) Standard Methods for Examination of Water and Waste Water 14th Ed., 1975. 419 LC. Cadmium Reduction Method (Tentative).

4) P. G. Brewer and J. P. Riley, "The Automatic Determination of Nitrate in Sea Water". Deep-Sea Research, 1965, Vol. 12, page 765.

5) Robert D. Cox, "Determination of Nitrate and Nitrite at the Parts per Billion Level by Chemiluminescence". Anal. Chem. 1980, 52, 332-335.

6) Robert C. Doerr, Jay B. Fox, Jr., Leon Lakritz, and Walter Fiddler, "Determination of Nitrite in Cured Meats by Chemiluminescence Detection". Anal Chem. 1981, 53, 381-384.

7) James E. O'Brien and Janece Fiore, "Automation in Sanitary Chemistry—Parts 1 and 2".

8) F. A. J. Armstrong, C. R. Stearns, and J. D. H. Strickland, "The Measurement of Unwelling and Subsequent Biological Processes By Means of the Technicon Autoanalyzer and Associate Equipment". Deep-Sea Research, 1967, Vol. 14, pages 381-389.

9) C. Garside, "A Chemiluminescent Technique for the Determination of Nanomolar Concentrations of Nitrate and Nitrite in Seawater". Marine Chemistry, 11 (1982), pages 159-167.

10) A. Henriksen and A. R. Selmer-Olsen, "Automatic Methods for Determining Nitrate and Nitrite in Water and Soil Extracts". Analyst, May, 1970, Vol. 95, pages 514-518.

11) Ted W. Walsh, "Total Dissolved Nitrogen in Seawater: a New-High-Temperature Combustion Method and a Comparison with Photo-Oxidation". Marine Chemistry, 26 (1989), pages 295-311.

12) ASTM Designation: D 1254-67 (reapproved 1974). Standard Methods of Test for Nitrite Ion in Water.

As a generalization, the procedures above do not provide either total nitrogen or constituent break outs from the total nitrogen. To the extent that they do provide either nitrate measurement only or nitrite measurement only, they are unable to provide the total bound nitrogen output.

SUMMARY OF THE INVENTION

The present disclosure sets forth both a method and apparatus which analyzes bound nitrogen; that is, it will provide or furnish total nitrogen and individual break outs representative of nitrites and nitrates in a water sample. To this end, a single apparatus is illustrated, but it is further illustrated with certain portions of the apparatus omitted to show only a nitrite analytical system, a nitrate analytical system, and a total nitrogen system. In other words, the three individual analytical sets of equipment are combined to provide a single set of equipment which is shown and described below. Furthermore, the equipment carries out the foregoing alternatively analytical routines so that totals are provided. By suitable arithmetic analysis of the data, the total nitrogen is first indicated and from that certain deductions are made by which one obtains three constituents which are total nitrates, total nitrites, and the total of other nitrogen compounds.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

Figure 1:
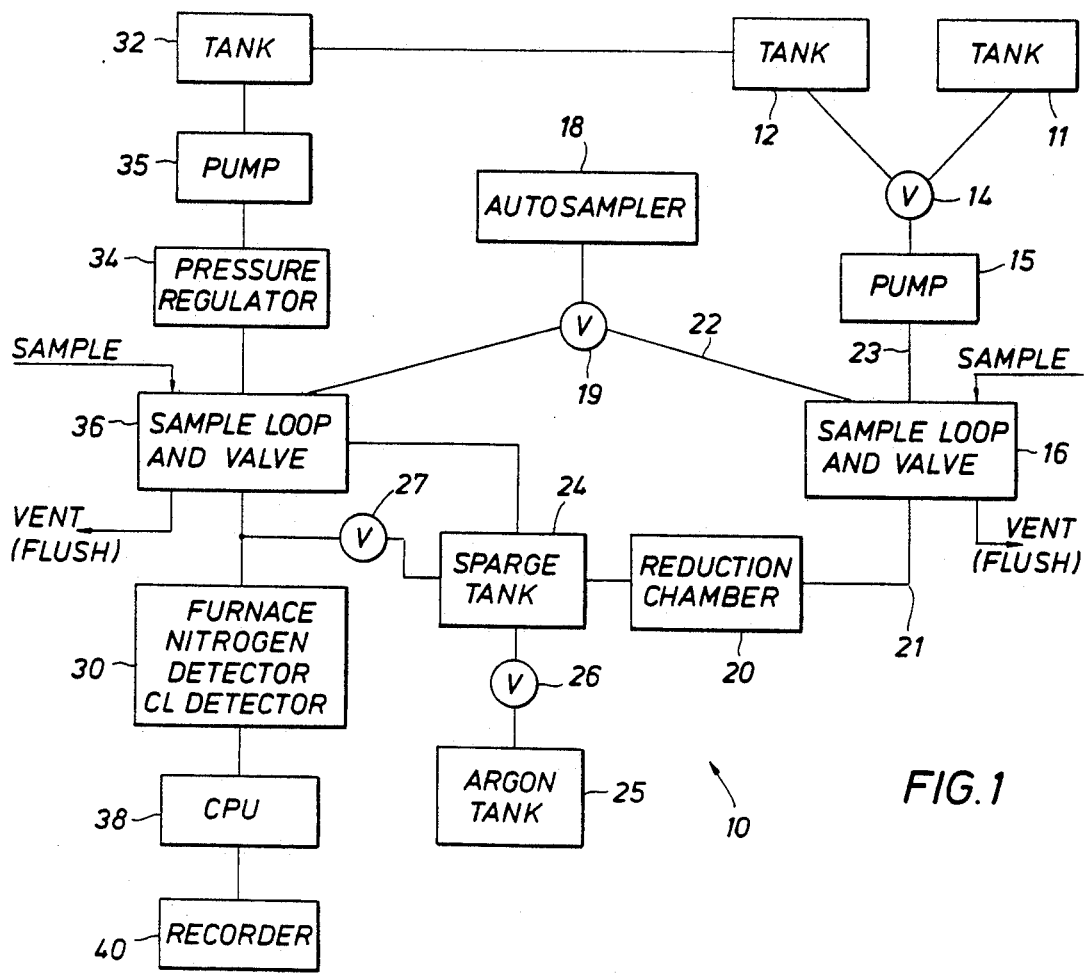
FIG. 1 is a flow diagram of a system of apparatus for testing for nitrogen in a specimen wherein multiple types of tests can be run to provide measurements of nitrogen content.

Attention is directed first to FIG. 1 of the drawings. In FIG. 1 of the drawings, a system is set forth and is indicated generally by the numeral 10 which refers to the entire system or apparatus which is shown in FIG. 1 of the drawings. Moreover, the system of FIG. 1 is a combined system of apparatus which makes separate measurement operations. The various measurements are output to a CPU and recorder so that the data is captured and is available for certain arithmetic operations as will be described. Therefore, beginning with FIG. 1, the description will set forth structural components and show how they connect together. In addition to that, FIGS. 2, 3, and 4 will then be described which take advantage of some but not all of the components. This break out will be used so that the individual test modes can be described and understood. Moreover, the descriptions of FIGS. 2, 3, and 4 will be enhanced with the description of the chemistry of the conversion. Exemplary equations will also be given whereby the test procedures can be more readily understood.

One must note that nitrogen is a polyvalent element. In view of this, and also to avoid confusion, the terms nitrate and nitrite refer to the ionic forms in solution, or to $NO_3-$ and also $NO_2-$. These are handled in solution as part of the sample delivered with a water carrier. This is a valuable feature of the present system. By contrast, there are various gas forms of $NO_x$, and this disclosure takes advantage of the fact that NO (nitric oxide) is a gas. One chance of confusion arises with $NO_2$, a gas; generally, this disclosure deals primarily with $NO_2-$, the ionic form of nitrogen containing compound, and not with $NO_2$, the oxide in gas form, That can be present in the total nitrogen measurement of the sample and will be measured if present.

In FIG. 1, the numeral 12 identifies a tank which holds a supply of pure water meaning water which has been deionized. This tank or supply will be used in certain steps to be described. There is another tank 11 provided with an aqueous solution of $NH_4Cl/EDTA$. Both of these tanks are connected to a three way valve 14 which provides an output of one or the other through a pump 15 which provides a specified pressure. As illustrated, all of the components in the present apparatus are connected by various and sundry flow lines. The flow lines are plumbed to the various components in suitable size and length to make the necessary connections. More importantly, the flow lines are formed of inert materials so that they do not interact with the constituents flowing in the lines. The pump therefore provides one or the other of the liquids from the tanks 11 or 12 pumped into a sample valve which is equipped with a measured sample loop. This valve and loop is indicated at 16. The sample loop is calibrated to a particular size such as 50 microliters. The system also includes an autosampler 18 which provides an output flow through a valve 19, and the valve 19 directs the output of the autosampler 18 through either of two lines. One of the lines extends to the sample valve 16. The sample valve 16 is a multiport valve switchable between two positions and having the sample loop connected between two of the ports. The sample of interest is introduced by the sample valve to fill the storage loop. There are two well accepted procedures for injection of the sample. One is by means of the autosampler 18. Another is injection through an injection port by means of a syringe. In any case, the sample loop is filled with the valve switched to one position, and the sample is then delivered out of the sample loop by switching to the other position to deliver sample through a line to a reduction chamber 20. For sake of clarity, it should be noted that the sample received at the reduction chamber 20 flows there through line 21. It is input from the autosampler by the flow line 22. Alternately, it is input by syringe (not shown) which injects into the sample valve for filling the storage loop. The line 23 provides one or the other of the two liquids from the tanks 11 and 12 under control of the valve 14 and this is used for other purposes to be described.

The reduction chamber is useful in converting nitrate to nitrite; this will be described in detail below. The numeral 24 identifies a sparge tank. It is provided with a flow of inert gas from a tank 25. One acceptable gas is helium and another is argon. This flow is metered through a sparge gas valve 26. That delivers the metered flow into the sparge tank 24. Flow from the tank 24 is directed outwardly to an outlet vale 27. The nitrogen detector 30 detects bound nitrogen in the sample delivered through the output valve 27.

Attention is momentarily directed to an additional tank 32 in FIG. 1 which holds a supply of pure water, again deionized water. It is connected with a pump 35 which is similar to the pump 15. That provides an output flow to a pressure regulator 34 which then connects with a sample valve with storage loop at 36. In turn, that connects by a supply line into the nitrogen detector 30.

As a matter of construction convenience and to hold down costs and complexity, the tanks 12 and 32 can be separate or can be one tank. In similar fashion, the pumps 15 and 35 can be the same pump or separate pumps which are duplicate devices. Likewise, the valves 16 and 36 can be duplicates, or a sinlge valve (with multiple ports) can be sued. For purposes of explanation, the present apparatus is illustrated in FIG. 1 to show two separate water tanks, two pumps, and two sample valves. Nevertheless, they can be connected precisely as illustrated or alternatively, single devices can used instead of the illustrated duplicate devices.

The system of FIG. 1 shows water sources cooperative with valves, pumps and pressure regulators; a sample is introduced at the sample loop 16 and is carried with the water flow. The water serves as a carrier, and flows through the indicated conduits as a result of the operation of the pumps illustrated in FIG. 1.

A suitable nitrogen detector is illustrated in the Parks patent mentioned above. Assume for purposes of example that a sample is input having a volume of 50 microliters and is tested. The total bound nitrogen in the sample is output from the nitrogen detector 30 to a CPU 38 and that data is transferred to a suitable recorder 40 such as a strip paper chart recorder. That output might indicate that the nitrogen content is a specific number such as 10 parts per million (ppm hereinafter).

Consider now the possibility of injecting a sample for testing in a different fashion and obtaining greater detail in the data.

Assume for purposes of illustration that the sample merely has chemically bound nitrogen and is represented by the symbol RN. The R refers generally to the rest of the molecule(s) in the sample. In that event, the nitrogen detector 30 executes the following two steps where the RN is exposed to oxygen to yield NO plus gases of combustion.

As seen in FIG. 1, the nitrogen detector includes a furnace. The NO gas is introduced into the nitrogen detector and the NO gas is subjected to an increase in temperature in the furnace. The second equation below shows how the NO is mixed with ozone which yields $NO_2^*$ in a conversion which is accompanied with emission of a quanta of measureable light. Note that metastable form (marked by an asterisk) has a life of less than one second, and probably is in the millisecond range. The two conversions are given by equations 1 and 2:

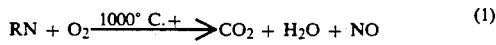

(1)

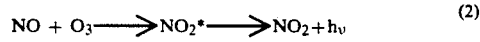

(2)

Assume however that the sample includes nitrates in it. In that instance, a different sequence of conversions is necessary. The nitrate is conducted through a first conversion to change the nitrate into a nitrite, and the nitrite is subsequently changed into NO. In a typical specimen including any of a variety of nitrate salts, the $NO_3-$ is first converted to $NO_2-$, and that is subsequently converted to NO. The first conversion occurs in the presence of a copper-cadmium catalyst causing formation of the $NO_2-$. As a second step, the $NO_2-$ is converted into NO in a conversion assisted by a mixture of two catalytic agents which are L-tartaric acid and also L-ascorbic acid.

The two conversions just mentioned as described in equations 3 and 4.

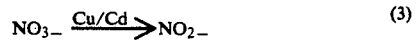

(3)

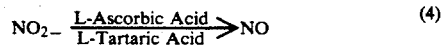

(4)

Figure 2:
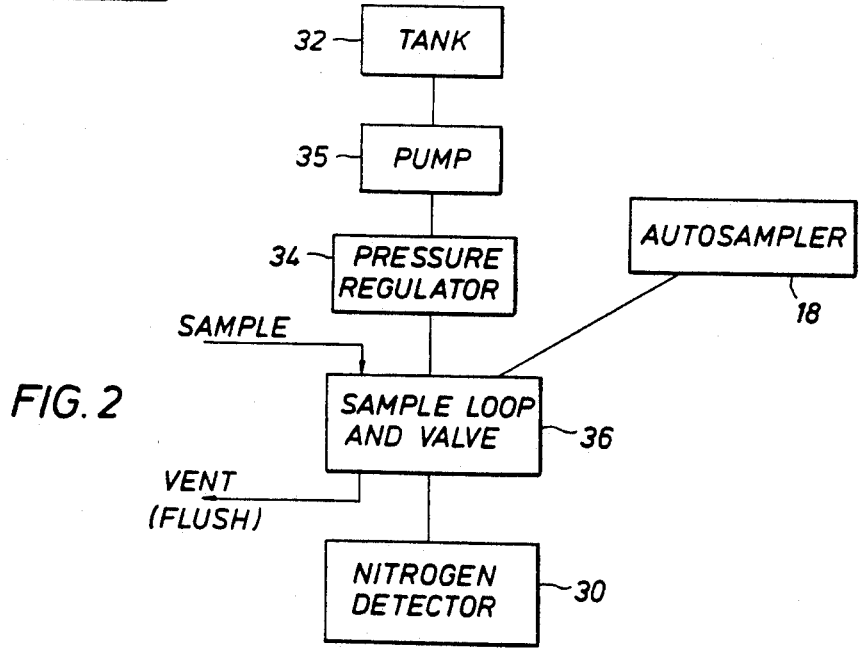
FIG. 2 is a portion of the apparatus shown in FIG. 1 for obtaining a measure of total nitrogen content.

Consider now operation of the present system. This is best illustrated and described by utilization of FIGS. 2, 3, and 4. For instance, FIG. 2 shows the system for making a total nitrogen analysis. In this instance, either through the use of a sample injection syringe cooperative with the sample valve 36 or through the autosampler 18, a sample is provided and input to the nitrogen detector 30. That provides the appropriate analysis and provides an output where the nitrogen is indicated in acceptable units either as a percentage of the sample or measured in ppm.

TOTAL NITROGEN ANALYSIS

FIG. 2 of the drawings shows certain other components from FIG. 1 which had been again illustrated while certain components had been omitted. This is a system which provides for total nitrogen analysis. Assume for purposes of example that the system is equipped with a 50 microliter sample loop which stores a sample or specimen. Moreover, this is loaded into the system by means of the autosampler 18, or alternately, through use of the sample valve 36 equipped with the requisite loop for metering the supply of sample. By means of the autosampler or through the use of a syringe, the necessary water solution of the sample is loaded. It is delivered into the sample loop and held in the sample storage loop momentarily. By proper manipulation of the sample valve 36, and by further operation of the pump 35, a fluid media is supplied which forces the sample out of the loop into the nitrogen detector. The fluid media that is supplied is from the tank 32. Preferably, this is water which is completely neutral and free of chemically bound nitrogen and which is sufficiently pure that it does not create an artificial base line. Assume for purposes of description that the supplied sample includes RN and also various salts of nitrate and nitrite. They are all input to the nitrogen detector and all are collectively consumed by this system which converts all the chemically bound nitrogen (e.g., nitrogen in the form of $NO_3-$, $NO_2-$, amines, $CN-$, etc.), and the total is output in the form of percent (%) or ppm depending on the calibration of the system. Note that there is no discrimination; note however that there is no false data derived from atmospheric nitrogen or nitrogen which might otherwise be dissolved in the sample. In other words, it is primarily an indication of bound nitrogen in compound form.

Figure 3:
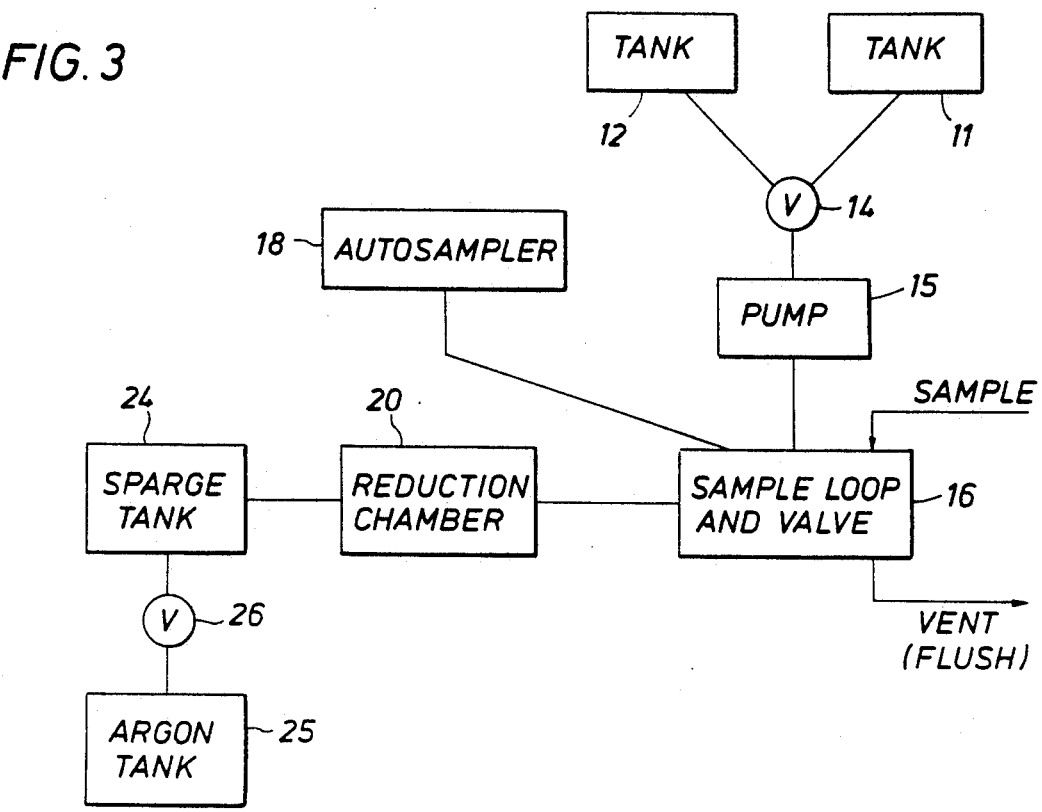
FIG. 3 is a portion of the apparatus shown in FIG. 1 for measuring the nitrate content.

Contrast FIG. 3 with FIG. 2. In FIG. 3, a nitrate bearing specimen is loaded. Again, the specimen is input through the use of an injection syringe at the sample valve and is placed in the storage loop, again having a representative capacity of 50 microliters. In an alternate mode of injection, the sample is delivered through the autosampler 18 and is conveyed to the sample valve 16 and is stored in the loop. The valve is operated in the well known manner, and in response to pump pressure which is applied through the pump 15, the sample is delivered along with a fluid flow media which is a water solution of $NH_4Cl/EDTA$ from the supply tank. Again, this water is neutral. It is first delivered through the chamber 20 and then into the chamber 24. In the chamber 20, there is a first conversion which occurs. The chamber 20 provides a serpentine flow path over an expanded surface area. The surface can be any suitable material so long as it is primarily inert and does not interact with the flowing sample. For instance, the surface area can be teflon coated, can be formed of glass, or can be most metal surfaces. Primarily, metal surfaces are acceptable provided they do not interact with the sample, and this is ordinarily the case. The surface areas however include partial coating with copper and cadmium. The copper and cadmium act as a catalyst. The chamber 20 thus provides a serpentine flow path which holds the sample flowing through it for a fraction of a second or longer. It is sufficiently long that the dwell time is perhaps one second or greater. The dwell time is not critical except that it be sufficient to cause conversion of the nitrate which conversion is in accordance with the teachings of equation 3 above.

Moreover, the chamber 20 is operated typically at ambient temperature, and hence no preheater or thermal jacket is required for the chamber 20. It operates primarily at ambient temperature and at sufficient pressure to provide throughput of the sample which flows with the flowing liquid media delivered through the pump 15. As will be understood, the connective lines are neutral in the choice of materials, and the pump pressure and throughput are sufficient to cause adequate flow into the chamber 20 and out of the chamber.

In the chamber, the equation 3 conversion occurs whereby $NO_3-$ is converted into $NO_2-$ by reduction. This then inputs the sample in the next stage of processing after reduction from the $NO_3-$. Assuming surface contact with an adequate surface area of the metal catalyst as mentioned, complete conversion occurs and no further $NO_3-$ remains in the sample. Rather, it is now all $NO_2-$. At this juncture, it is introduced into the sparge tank 24 where $NO_2-$ derives from two sources. That is, it includes $NO_2-$ which was originally in the sample, and it also includes all the nitrate after conversion to the nitrite form by reduction in the chamber 20.

The chamber 24 is operated substantially at ambient temperature and has a slightly elevated internal pressure as a result of introducing a sparge gas from the tank through the valve 26. Bubbling and agitation occurs in the chamber. This chamber is a liquid chamber which is partially filled with liquid, and the sample which is introduced flows with a liquid stream also. In the chamber, the pressurized gas from the gas tank is permitted to bubble up through the tank and flows out through the top flow line. Reduction of the nitrite occurs in the tank 24 and produces NO. At the pressures and temperatures that are apt for operation of the tank 24, NO is only in the gaseous form. Therefore, it is able to escape the tank 24. The tank is initially charged with water holding the catalytic acids mentioned above. This catalytic agent in the liquid remains in the tank 24. The sample which is introduced from the reduction chamber 20 is also liquid. Coupled with the sparging which occurs as the gas bubbles up through the tank, there is a gas discharge flow out of the tank 24 which includes the inert gas from the tank 25 and this carries with it the NO in gaseous form. As will be understood, the foregoing typically occurs at ambient temperatures, and the pressure within the tank 24 is several psi above atmospheric to assure that there is a pressure drive which carries the gas flow out of the tank 24. This gaseous drive is then delivered to the nitrogen detector 30. It then makes the conversion so that the NO which is in the gas flow to the detector 30 is oxidized whereby all the NO is measured. At this juncture, the detector 30 will form an output signal. Note however that this output signal is indicative of conversion of nitrates and nitrites into NO. For instance, if the sample in the sequence described with regard to FIG. 3 includes water soluble amines, they will remain in the tank 24. The nitrates and nitrites will be converted into the gaseous form and escape for subsequent detection and measurement. But, those which are in solid or liquid form and which do not vaporize remain in the tank 24. This enables a sample to be converted whereby only the combination of nitrates and nitrites are output as bound nitrogen constituents and the measure thereby indicates the sum of the two. This will be discussed in detail below.

Figure 4:
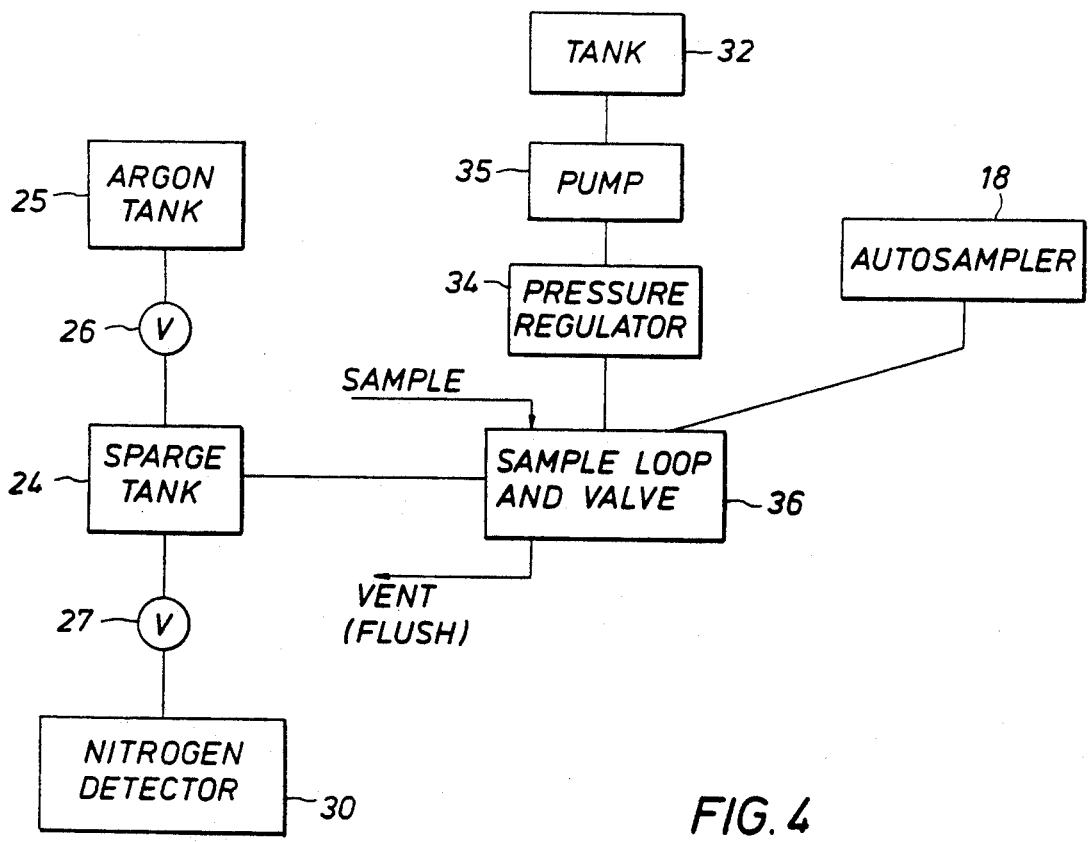
FIG. 4 is a portion of the apparatus shown in FIG. 1 for providing nitrite measurement.

FIG. 4 shows the use of the apparatus solely for the detection of nitrite in the sample. Again, the tank 32 which provides water is utilized and is delivered by the pump 35. This is input to the sample valve 36. As before, the sample valve is loaded either by syringe or by autosampler to fill the sample loop, and this is preferably filled so that it can be delivered by deionized water from the tank 32. This flow is directed into the sparge tank 24; the reduction chamber 20 is not needed for this conversion. As before, any nitrite is converted into NO in gaseous form which is removed from the sparge tank along with the flow of argon or helium gas as a carrier to the nitrogen detector. Moreover, in the next stage, the same conversion again occurs as mentioned before. If there are any other bound nitrogen constituents in the sample, they remain in the liquid and are trapped in the sparge tank. Accordingly, the output represents a measure of nitrite only.

Putting the foregoing steps together and assuming that one wishes to obtain a test of constituent components in a sample, assume for purposes for description that a sample is supplied of perhaps 10 or more milliliters. This sample is broken up into individual measured or metered segments of 50 microliters each. This presupposes the use of a sample loop of 50 microliters size. First, a 50 microliter sized sample is delivered and a total output is obtained for all nitrogen constituents contained in the sample. This is accomplished using the arrangement of equipment which is shown in FIG. 2. It completely circumvents the reduction chamber 20 and does not use the sparge tank 24. It will provide a measure of bound nitrogen in all aspects including nitrates, nitrites, and various oxides of nitrogen. This will be accomplished merely by delivery of the sample flowing with deionized water into the nitrogen detector 30. Assume for purposes of description that the output is 1200 ppm for that sample.

Next, another measured portion of 50 microliters is again separated from the larger sample and is delivered through the system of FIG. 3. In this approach, any nitrates which are found in the sample are converted into nitrites, and the output provides a measure which is the sum of both nitrates and nitrites. Assume for purposes of description that this provides an output of 500 ppm. This will represent the sum of the two, namely the nitrate and nitrite constituents.

A third sample again of 50 microliters is measured from the larger sample and is tested in the routine shown in FIG. 4. When tested, it provides an output which is indicative of nitrites only, and assume that this is 300 ppm. Recalling that 500 ppm were measured for the sum of nitrates and nitrites, this indicates that the nitrite constituent is 300 ppm and the nitrate part is only 200 ppm. The remaining 700 ppm derives from other nitrogen containing compounds.

One of the advantages of the present system is that the catalysts are preserved during the analytical run. Conveniently, FIG. 1 shows a tank which provides a mixture including EDTA. This is a chelating agent which is well known as a metal chelate. It isolates interfering metals by tying up any metal ions such as iron, etc. They are removed from possible interaction occurring in the chambers 20 and 24. It assures that the system does not become slowly poisoned. The EDTA is permitted to flow through the system for this purpose to particularly charge the reduction chamber 20 on a continuing basis and by clearing away any available metal ions which might otherwise slow down the reaction or which might otherwise tie up the anions to which the present process responds. In addition to that, the $NH_4Cl$ in water solution also does the same thing by making available a cation which is readily soluble in water and which will enhance ionic transfer with the fluid flow which ultimately ends up in the sparging tank 24. In the sparging tank, the ammonium chloride buffered solution will nevertheless permit the nitrites in that solution to be selectively reduced so that NO is liberated in gaseous form for subsequent processing.

The internal surfaces are preferably inert in all vessels and tubing which is used for the apparatus. If desired, it may be helpful to add pressure regulators at various locations. Generally, the pressures that are accomplished are sufficient to cause fluid flow, and excessive pressures need not be accomplished. To the extent that the system holds trapped water for any period of time, there is the possibility of bacteria growth in the water which might create undesirable conversions. To this end, it may be helpful to either cleanse and sterilize the water periodically, or if the water is to be left in the system for a long time, incorporate such equipment as will be necessary to prevent this. This can be understood and readily accomplished without difficulty.

As seen in the process where the liquid carrier (mostly water) flows into the sparge tank, the water is left in the tank and the sample constituents formed of nitrogen are separated as gas; this is tested devoid of excess water. In testing the sample flowing in a water based carrier (in FIG. 2) where total nitrogen is tested, the flow of water may be excessive and will enter the nitrogen detector 30. The excess water may create difficulties in testing; accordingly, the amount of water is reduced by installing a water trap in advance of the nitrogen detector 30. One approach is water reduction by distillation, or perhaps by membrane separation.

As a practical matter, the EDTA chelate is the preferred form but other chelate agents are known. Also, the organic acids are preferred because they are generally safer to handle; but inorganic acids will also suffice even though they are more dangerous to handle.

While the foregoing is directed to the preferred embodiment, the scope thereof is determined by the claims which follow.

What is claimed is:

1. A method of treating an aqueous test sample in a test system having a test sample receiving means connected to deliver a test sample for testing in a chemiluminescent test chamber forming a light emission observed and measured by a light responsive output means to analyze for chemically bound nitrogen contained in said test sample comprising the steps of:
    (a) forming from said test sample three (3) smaller samples having essentially equal volume and chemical composition;
    (b) submitting a first smaller sample in the test system to oxidizing conditions sufficient to convert the total chemically bound nitrogen in said first small sample to form $NO_x$;
    (c) converting said $NO_x$ to NO and subsequently to $NO_2^*$ which decays to be ground state accompanied by emission of quanta of light thereby performing a chemiluminescent measurement of said emission of light and determining total chemically bound nitrogen in said first smaller sample;
    (d) carrying a second smaller sample through a selective reduction step in aqueous solution to reduce any $NO_2-$ therein to NO gas, and thereafter converting said NO to $NO_2^*$ thereby performing a chemiluminescent measurement and determining total $NO_2-$ in said second smaller sample;
    (e) carrying a third smaller sample through a selective reduction step in aqueous solution to reduce any $NO_3-$ therein to $NO_2-$ and thereafter treating said third smaller sample to convert said $NO_2-$ to NO gas and subsequently to convert said NO gas to $NO_2^*$ performing a chemiluminescent measurement and determining total $NO_3-$ in said third smaller sample; and
    (f) forming measurement data outputs representing total bound nitrogen, total $NO_2-$, total $NO_3-$, and other nitrogen compounds in the original test sample.

2. The method of claim 1 wherein each selective reduction from $NO_2-$ to NO occurs in a manner such that all NO gas is directed into a chamber for conversion to $NO_2^*$ in the test system thereby enabling a chemiluminescent measurement of total $NO_2-$.

3. The method of claim 2 wherein each selective reduction is carried out in the test system by directing the sample into an aqueous solution in the test system containing an effective amount of ascorbic or tartaric acid, or a mixture thereof and the NO gas is removed from said aqueous solution by sparging with an inert carrier gas.

4. The method of claim 1 wherein the selective reduction from $NO_3-$ to $NO_2-$ is accomplished in a reduction chamber in the presence of an appropriate metal catalyst.

5. The method of claim 1 wherein the selective reduction to reduce $NO_3-$ to $NO_2-$ is accomplished in a first chamber after which the sample is directed into a second chamber for conversion of the $NO_2-$ to NO gas.

6. A method of testing a test sample in a test system having a test sample receiving means connected to deliver a test sample for testing in a chemiluminescent test chamber forming a light emission observed and measured by a light responsive output means including chemically bound nitrogen comprising the steps of:
    (a) in the test system, converting by oxidation a sample having a specified size to form $NO_x$;
    (b) measuring the $NO_x$ by conversion to NO and then converting NO to $NO_2^*$ which decays to the ground state accompanied by emission of quanta of light in the chemiluminescent test chamber and performing a chemiluminescent measurement and determining chemically bound nitrogen;
    (c) measuring in a second and equal sized sample only $NO_2-$ to obtain a measurement of $NO_2-$ wherein the $NO_2-$ measurement step includes:
        (1) reducing the $NO_2-$ to form NO in gaseous form;
        (2) delivering the gaseous form NO to a nitrogen detector; and
        (3) converting the NO to $NO_2^*$ and performing a chemiluminescent measurement and determining $NO_2-$;
    (d) measuring in a third and equal sized sample $NO_3-$ and obtaining a measurement of $NO_3-$; and (e) forming measurement data outputs of total bound nitrogen and subtotals of $NO_2-$, $NO_3-$ and other nitrogen compounds in the total.

7. The method of claim 6 wherein the reduction from $NO_2-$ to NO occurs in a liquid solution in a container in the test system and forms NO released in gas form to flow from the container so that all of the NO is directed to a test chamber in the test system for testing in a process converting NO into $NO_2*$ accompanied by emission of a quanta of light.

8. The method of claim 7 wherein an acidic reducing agent is placed in a water solution of the sample in a container in the test system including $NO_2-$ and the water solution in the container is stirred by sparging an inert carrier gas through the solution converting $NO_2-$ to NO and said carrier gas carrying NO away as a gas.

9. The method of claim 8 wherein the water solution includes ascorbic or tartaric acid, or a mixture thereof.

10. The method of claim 8 wherein the sample including $NO_2-$ flows with a water carrier from said sample loop to a sparge tank.

11. The method of claim 6 wherein sample including $NO_3-$ is:
    (a) first reduced by catalytic conversion from $NO_3-$ to $NO_2-$; and
    (b) then reducing the $NO_2-$ to NO in gas form.

12. The method of claim 6 including:
    (a) injecting the specific sized sample $NO_3-$ into a flowing carrier water to enable sample measurement;
    (b) directing the carrier flows into a first chamber in the test system having an agent therein reducing any $NO_3-$ to $NO_2$;
    (c) then directing the carrier flow into a second chamber in the test system having an agent therein reducing any $NO_2-$ to NO;
    (d) delivering NO to a nitrogen detector so that NO is separated from water in the carrier flow by heating in a furnace to enable measurement of NO only; and
    (e) forming an output measurement of NO in the sample and separately indicating in the measurement the portions attributed to $NO_3-$ and $NO_2-$.

13. A method of converting chemically bound nitrogen in a test sample in a test system having a test sample receive means connected to deliver a test sample for testing in a chemiluminescent test chamber forming a light emission observed and measured by a light responsive output means into NO to enable nitrogen measurement comprising the steps of:
    (a) measuring a specified size of sample material from a sample having $NO_3-$ therein, and making an intermediate and subsequent reduction of the measured sample to obtain $NO_2-$ and then NO;
    (b) measuring the NO and expressing the NO measure in acceptable units of measure wherein the NO is measured by chemiluminescent conversion in the test system $NO_2*$ accompanied with measurable light emission;
    (c) separately from steps a and b, from the same sample material, measuring the same specified size of sample suspected of having $NO_2-$ therein, and making a reduction to convert $NO_2-$ to NO;
    (d) measuring the NO from step (c) above and expressing the NO measure in the same units of measure of step (b);
    (e) from the sample material suspected of having chemically bound nitrogen therein, making a measurement of the bound nitrogen and expressing the bound nitrogen measurement in the same units of measurement of step (b); and
    (f) representing the total bound nitrogen as three subtotals which are $NO_3-$, $NO_2-$, and other bound nitrogen compounds and wherein the three subtotals represent the total bound nitrogen in the sample material.

14. The method of claim 13 wherein three equally sized samples of the material are formed and separately tested to provide three measurements, and the three measurements of steps (b), (d), and (e) represent the subtotals.

15. The method of claim 13 wherein the total measurement of bound nitrogen is separately measured; wherein the $NO_2-$ subtotal is separately measured; wherein the $NO_3-$ is converted to $NO_2-$ and is measured in the presence of $NO_2-$ of the sample; and subtracting the $NO_2-$ subtotal from the total bound nitrogen to obtain $NO_3-$ in the sample.

* * * * *

UNITED STATES PATENT AND TRADEMARK OFFICE
CERTIFICATE OF CORRECTION

PATENT NO. : 5,300,441
DATED : Apr. 5, 1994
INVENTOR(S) : Eugene M. Fujinari, et al It is certified that error appears in the above-indentified patent and that said Letters Patent is hereby corrected as shown below:

Title page, Other Publications, line 7, after the word "Water" change the word "adn" to --and--;

Title page, Abstract, line 4, after the word "total" change the words "nitrogen bound" to --bound nitrogen--;

Title page, Abstract, line 8, change the word "nitrate" to --nitrite--;

Title page, Abstract, line 12, after the word "method" insert the word --first--

Title page, Abstract, line 12 and after the word "a" delete the word "first"·

Title page, Abstract, line 15, change "($NO_2$)" to --($NO_2^-$)--;

Title page, Abstract, line 15, change "nitrile" to --nitrite--;

Column 1, line 55, change "($NO_3$—)" to --($NO_3^-$)--;

Column 1, line 58, change "($NO_2$—)" to --($NO_2^-$)--;

Column 3, line 25, after the word "nitrate" insert the words --and nitrite--;

UNITED STATES PATENT AND TRADEMARK OFFICE
CERTIFICATE OF CORRECTION

PATENT NO. : 5,300,441
DATED : Apr. 5, 1994
INVENTOR(S) : Eugene M. Fujinari, et al It is certified that error appears in the above-indentified patent and that said Letters Patent is hereby corrected as shown below:

Column 3, line 54, change "($NO_3$—)" to --($NO_3^-$)--;

Column 3, line 54, change "($NO_2$—)" to --($NO_2^-$)--;

Column 3, line 61, change "($NO_2$—)" to --($NO_2^-$)--;

Column 4, line 48, change "vale" to --valve--;

Column 4, line 65, change "sued" to --used--;

Column 5, line 2, after the word "can" insert the word --be--;

Column 5, line 50, change "($NO_3$—)" to --($NO_3^-$)--;

Column 5, line 50, change "($NO_2$—)" to --($NO_2^-$)--;

UNITED STATES PATENT AND TRADEMARK OFFICE
CERTIFICATE OF CORRECTION

PATENT NO. : 5,300,441

DATED : Apr. 5, 1994

INVENTOR(S) : Eugene M. Fujinari, et al

It is certified that error appears in the above-indentified patent and that said Letters Patent is hereby corrected as shown below:

Column 5, line 53, after the phrase "formation of the", change "($NO_2$—)" to --($NO_2^-$)--;

Column 5, line 53, after the phrase "second step, the", change "($NO_2$—)" to --($NO_2^-$)--;

Column 5, line 60, change "($NO_3$—)" to --($NO_3^-$)--;

Column 5, line 60, change "($NO_2$—)" to ($NO_2^-$)--;

Column 5, line 63, change "($NO_2$—)" to ($NO_2^-$)--;

Column 6, line 23, change "loop" to --valve--;

Column 6, line 38, change "($NO_3$—)" to --($NO_3^-$);

Column 6, line 38, change "($NO_2$—)" to --($NO_2^-$)--;

Column 6, line 38, change "(CN—)" to --($CN^-$)--;

Column 7, line 20, change "($NO_3$—)" to --($NO_3^-$)--;

UNITED STATES PATENT AND TRADEMARK OFFICE
CERTIFICATE OF CORRECTION

PATENT NO. : 5,300,441          Page 4 of 10
DATED : Apr. 5, 1994
INVENTOR(S) : Eugene M. Fujinari, et al It is certified that error appears in the above-indentified patent and that said Letters Patent is hereby corrected as shown below:

Column 7, line 20, change "($NO_2$—)" to --($NO_2^-$)--;

Column 7, line 22, change "($NO_3$—)" to --($NO_3^-$)--;

Column 7, line 25, change "($NO_3$—)" to --($NO_3^-$)--;

Column 7, line 26, change "($NO_2$—)" to --($NO_2^-$)--;

Column 7, line 27, change "($NO_2$—)" to --($NO_2^-$)--;

Column 7, line 28, change "($NO_2$—)" to --($NO_2^-$)--;

Column 10, line 5, change "($NO_2$—)" to --($NO_2^-$)--;

Column 10, line 8, change "($NO_2$—)" to --($NO_2^-$)--;

Column 10, line 11, change "($NO_3$—)" to --($NO_3^-$)--;

Column 10, line 11, change "($NO_2$—)" to --($NO_2^-$)--;

Column 10, line 12, change "($NO_2$—)" to --($NO_2^-$)--;

UNITED STATES PATENT AND TRADEMARK OFFICE
CERTIFICATE OF CORRECTION

PATENT NO. : 5,300,441
DATED : Apr. 5, 1994
INVENTOR(S) : Eugene M. Fujinari, et al It is certified that error appears in the above-indentified patent and that said Letters Patent is hereby corrected as shown below:

Column 10, line 18, change "($NO_2$—)" to --($NO_2^-$)--;

Column 10, line 18, change "($NO_3$—)" to --($NO_3^-$)--;

Column 10, line 22, change "($NO_2$—)" to --($NO_2^-$)--;

Column 10, line 25, change "($NO_2$—)" to --($NO_2^-$)--;

Column 10, line 34, change "($NO_3$—)" to --($NO_3^-$)--;

Column 10, line 34, change "($NO_2$—)" to --($NO_2^-$)--;

Column 10, line 38, change "($NO_3$—)" to --($NO_3^-$)--;

Column 10, line 38, change "($NO_2$—)" to --($NO_2^-$)--;

Column 10, line 40, change "($NO_2$—)" to --($NO_2^-$)--;

UNITED STATES PATENT AND TRADEMARK OFFICE
CERTIFICATE OF CORRECTION

PATENT NO. : 5,300,441
DATED : Apr. 5, 1994
INVENTOR(S) : Eugene M. Fujinari, et al It is certified that error appears in the above-indentified patent and that said Letters Patent is hereby corrected as shown below:

Column 10, line 57, before the phrase "to obtain", change "($NO_2$—)" to --($NO_2^-$)--;

Column 10, line 57, after the phrase "measurement of", change "($NO_2$—)" to --($NO_2^-$)--;

Column 10, line 58, change "($NO_2$—)" to --($NO_2^-$)--;

Column 10, line 59, change "($NO_2$—)" to --($NO_2^-$)--;

Column 10, line 65, change "($NO_2$—)" to --($NO_2^-$)--;

Column 10, line 67, before the phrase "and obtaining", change "($NO_3$—)" to --($NO_3^-$)--;

Column 10, line 67, after the phrase "measurement of", change "($NO_3$—)" to --($NO_3^-$)--;

UNITED STATES PATENT AND TRADEMARK OFFICE
CERTIFICATE OF CORRECTION

PATENT NO. : 5,300,441        Page 7 of 10
DATED : Apr. 5, 1994
INVENTOR(S) : Eugene M. Fujinari, et al It is certified that error appears in the above-indentified patent and that said Letters Patent is hereby corrected as shown below:

Column 11, line 2, change "($NO_2$—)" to --($NO_2^-$)--;

Column 11, line 2, change "($NO_3$—)" to --($NO_3^-$)--;

Column 11, line 5, change "($NO_2$—)" to --($NO_2^-$)--;

Column 11, line 13, change "($NO_2$—)" to --($NO_2^-$)--;

Column 11, line 15, change "($NO_2$—)" to --($NO_2^-$)--;

Column 11, line 20, change "($NO_2$—)" to --($NO_2^-$)--;

Column 11, line 23, change "($NO_3$—)" to --($NO_3^-$)--;

Column 11, line 24, change "($NO_3$—)" to --($NO_3^-$)--;

Column 11, line 25, change "($NO_2$—)" to --($NO_2^-$)--;

Column 11, line 26, change "($NO_2$—)" to --($NO_2^-$)--;

Column 11, line 28, change "($NO_3$—)" to --($NO_3^-$)--;

UNITED STATES PATENT AND TRADEMARK OFFICE
CERTIFICATE OF CORRECTION

PATENT NO. : 5,300,441

DATED : Apr. 5, 1994

INVENTOR(S) : Eugene M. fujinari, et al

It is certified that error appears in the above-indentified patent and that said Letters Patent is hereby corrected as shown below:

Column 11, line 33, change "($NO_3$—)" to --($NO_3^-$)--;

Column 11, line 33, change "($NO_2$—)" to --($NO_2^-$)--;

Column 11, line 36, change "($NO_2$—)" to --($NO_2^-$)--;

Column 11, line 43, change "($NO_3$—)" to --($NO_3^-$)--;

Column 11, line 43, change "($NO_2$—)" to --($NO_2^-$)--;

Column 12, line 1, change "receive" to --receiving--;

Column 12, line 4, change "into" to --for--;

Column 12, line 7, change "($NO_3$—)" to --($NO_3^-$)--;

Column 12, line 9, change "($NO_2$—)" to --($NO_2^-$)--;

Column 12, line 17, change "($NO_2$—)" to --($NO_2^-$)--;

Column 12, line 18, change "($NO_2$—)" to --($NO_2^-$)--;

UNITED STATES PATENT AND TRADEMARK OFFICE
CERTIFICATE OF CORRECTION

PATENT NO. : 5,300,441
DATED : Apr. 5, 1994
INVENTOR(S) : Eugene M. Fujinari, et al It is certified that error appears in the above-indentified patent and that said Letters Patent is hereby corrected as shown below:

Column 12, line 28, change "($NO_3$—)" to --($NO_3^-$)--;

Column 12, line 28, change "($NO_2$—)" to --($NO_2^-$)--;

Column 12, line 39, change "($NO_2$—)" to --($NO_2^-$)--;

Column 12, line 40, change "($NO_3$—)" to --($NO_3^-$)--;

Column 12, line 40, change "($NO_2$—)" to --($NO_2^-$)--;

Column 12, line 41, change "($NO_2$—)" to --($NO_2^-$)--;

Column 12, line 42, change "($NO_2$—)" to --($NO_2^-$)--;

UNITED STATES PATENT AND TRADEMARK OFFICE
CERTIFICATE OF CORRECTION

PATENT NO. : 5,300,441
DATED : Apr. 5, 1994
INVENTOR(S) : Eugene M. Fujinari, et al It is certified that error appears in the above-indentified patent and that said Letters Patent is hereby corrected as shown below:

Column 12, line 43, change "($NO_3$—)" to --($NO_3^-$)--;

Signed and Sealed this

Fifth Day of December, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,300,441
DATED : April 5, 1994
INVENTOR(S) : Eugene M. Fujinari and Allen J. Britten It is certified that error appears in the above-indentified patent and that said Letters Patent is hereby corrected as shown below:

Column 10, line 15, change "(total $NO_3-$)" to -- the combined amount of $NO_3^-$ and $NO_2^-$ --;

Column 12, lines 43-44, change "(total bound nitrogen)" to -- combined amount of $NO_3^-$ and $NO_2^-$ --.

Signed and Sealed this

Twenty-eighth Day of May, 1996

Attest:

BRUCE LEHMAN

*Attesting Officer*     *Commissioner of Patents and Trademarks*